(12) United States Patent
Fishman et al.

(10) Patent No.: US 7,589,075 B2
(45) Date of Patent: Sep. 15, 2009

(54) USE OF AN ADENOSINE A3 RECEPTOR AGONIST FOR INHIBITION OF VIRAL REPLICATION

(75) Inventors: Pnina Fishman, Herzliya (IL); Kamel Khalili, Merion, PA (US)

(73) Assignee: Can-Fite Biopharma Ltd., Petach Tikva (IL)

( * ) Notice: Subject to any disclaimer, the term of this patent is extended or adjusted under 35 U.S.C. 154(b) by 474 days.

(21) Appl. No.: 10/466,263

(22) PCT Filed: Jan. 13, 2002

(86) PCT No.: PCT/IL02/00028

§ 371 (c)(1),
(2), (4) Date: Jan. 15, 2004

(87) PCT Pub. No.: WO02/055085

PCT Pub. Date: Jul. 18, 2002

(65) Prior Publication Data

US 2004/0106572 A1    Jun. 3, 2004

Related U.S. Application Data

(60) Provisional application No. 60/261,659, filed on Jan. 16, 2001.

(51) Int. Cl.
*A61K 31/52* (2006.01)
*A61K 31/522* (2006.01)
*A61K 31/7076* (2006.01)

(52) U.S. Cl. ................ 514/45; 514/263.23; 514/263.3; 514/263.35; 514/263.36

(58) Field of Classification Search ................ None
See application file for complete search history.

(56) References Cited

U.S. PATENT DOCUMENTS

| | | | |
|---|---|---|---|
| 5,443,836 | A | 8/1995 | Downey et al. |
| 5,573,772 | A | 11/1996 | Downey et al. |
| 5,688,774 | A | 11/1997 | Jacobson et al. |
| 5,773,423 | A | 6/1998 | Jacobson et al. |
| 6,048,865 | A | 4/2000 | Baraldi |
| 2007/0149462 | A1* | 6/2007 | Iyer et al. ............ 514/26 |

FOREIGN PATENT DOCUMENTS

| | | |
|---|---|---|
| WO | WO 94/21195 A1 | 9/1994 |
| WO | WO 95/02604 A1 | 1/1995 |
| WO | WO 99/06053 A1 | 2/1999 |
| WO | WO 99/20284 A1 | 4/1999 |
| WO | WO 01/19360 A2 | 3/2001 |

OTHER PUBLICATIONS

Zhou QY, Li C, Olah ME, Johnson RA, Stiles GL, Civelli O. "Molecular cloning and characterization of an adenosine receptor: the A3 adenosine receptor." Proc Natl Acad Sci U S A. Aug 15, 1992;89(16):7432-6.*

Thomas CA, Weinberger OK, Ziegler BL, Greenberg S, Schieren I, Silverstein SC, El Khoury "Human immunodeficiency virus-1 env impairs Fc reception-mediated phagocytosis via a cyclic adenosine monophosphate-dependent mechanism." J.Blood. Nov 1, 1997;90(9):3760-5.*

Osborn et. al. Tumor Necrosis Factor α and Interleukin 1 Stimulate the Human Immunodeficiency Virus Enhancer by Activation of the Nuclear Factor κB. Proceedings of the National Academy of Sciences of the United States of America, vol. 86, No. 7. (Apr. 1, 1989), pp. 2336-2340.*

Sajjadi, et al. Inhibition of TNF-a Expression by Adenosine: Role of A3 Adenosine ReceptorsJ Immunol, 1996, 156: 3435-3442.*

Shneyvays, et al. Induction of Apoptosis in Cardiac Myocytes by an A3 Adenosine Receptor Agonist. Exp Cell Res. 1998; 243:383-397.*

9-Nitocamptothecin Inhibits HIV-1 Replication in Human Peripheral Bloood Lymphocytes: A Potential Alternative for HIV-Infection/ AIDS Therapy. J Med. Virol. 2001; 64:238-244.*

Hasko, et al. Adenosine Receptor Agonists Difierentially Regulate Il-10, TNF-a, and Nitric Oxide Production in RAW 264.7 Macrophages and in Endotoxemic Mice. The Iournal of Immunology, 1996,157: 4634-4640.*

Bouma, Maarten; "Differential Regulatory Effects of Adenosine on Cytokine Release by Activated Human Monocytes"; Journal of Immunology. 1994; 4159-4167.

Gartner, Suzanne; "Virus Isolation and Production", Basic Virologic Techniques. Immunology Department, Primate Research Institute, New Mexico State University. 1990, 53-70.

Gilbertsen, R.; "Adenosine and Adenosine Receptors in Immune Function. Minireview and meeting report", Agents and Actions. 1987, vol. 22, 1/2, 91-98.

Gonzalez, Fernando; "Activation of Early Events of Mitogenic Response by a $P_{2y}$ Purinoceptor with Covalently Bound 3'-O-(4-benzoyl)-benzoyladenosine 5'-triphosphate", Proc. Natl. Acad. Sci. Dec. 1990 vol. 87, 9717-9721.

Linden, Joel; "Structure and Function of $A_1$ Adenosine Receptors"; The FASEB Journal. Sep. 1991, vol. 5, 2668-2675.

Pastan, Ira; "Role of Cyclic Nucleotides in Growth Control", Laboratory of Molecular Biology. Nation Cancer Institute, National Institutes of Health. 1975, 491-522.

Rozengurt, Enrique; "Adenosine Receptor Activation in Quiescent Swiss 3T3 Cells"; Experimental Cell Research. 1982, vol. 139; 71-78.

(Continued)

*Primary Examiner*—Mary E Mosher
*Assistant Examiner*—Stuart W Snyder
(74) *Attorney, Agent, or Firm*—Browdy and Neimark, P.L.L.C.

(57) ABSTRACT

The present invention concerns the use of an active ingredient selected from the group consisting of agonists of the adenosine receptor system, for inhibiting viral replication in cells. In particular, the invention provides a composition and method for inhibiting viral replication in cells, the method comprising presenting to the cells an effective amount of the active ingredient. According to one embodiment, the adenosine agonist is an A3 receptor agonist (A3RAg). The invention is particularly useful, for although not limited to, inhibiting the replication of HIV virus in human cells.

16 Claims, No Drawings

OTHER PUBLICATIONS

Sandber, G.; "Regulation of Thymocyte Proliferation: Effects of L-Alanine, Adenosine and Cyclic AMP in vitro". Thymus. 1981; vol. 3,63-75.

Söderbäck, U.; "Anti-aggregatory Effects of Physiological Concentrations of Adenosine in Human Whole Blood as Assessed by Filtragometry", Clinical Science. 1991, vol. 81, 691-694.

Stiles, Gary; "Adenosine Receptors and Beyond: Molecular Mechanisms of Physiological Regulation", Clinical Research. 1989, 12-18.

Stolfi, Robert; "Modulation of 5-Fluorouracil-induced Toxicity in Mice with Interferon of with the Interferon Inducer, Polyinosinic-Polycytidylic Acid", Cancer Research. Feb. 1983, 561-566.

Csaba Szabo et al., "Suppression of macrophage inflammatory protein (MIP)-1α production and collagen-induced arthritis by adenosine receptor agonists", British Journal of Pharmacology, (1998) 125, 379-387.

Calabrese et al., "Safety of antitumour necrosis factor (anti-TNF) therapy in patients with chronic viral infections: Hepatitis C, hepatitis B, and HIV infection" Ann Rheum Dis. 63:18-24 (2004).

Sha et al., "Effect of etanercept (Enbrel) on interleukin 6, tumor necrosis factor alpha, and markers of immune activation in HIV infected subjects receiving interleukin 2" AIDS Res Hum Retroviruses. 18(9):661-5 (2002).

Brabers et al., "Role of the proinflammatory cytokines TNF-α and IL-1β in HIV-associated dementia Nottet" European Journal of Clinical Investigation. 36:447-458 (2006).

Hermida-Escobedo et al., "A double-blinded clinical trial to assess the effect of pentoxifylline in the inhibition of tumor necrosis factor production in patients with AIDS" Int Conf AIDS. Jul. 7-12; 11: 123 (1996).

Okeoma et al., "APOBEC3 inhibits mice mammary tumor virus replication in vivo," Nature. 445:927-930 (2007).

Siekmann and Lawson, "Notch signaling limits angiogenic cell behavior in developing zebra fish arteries," Nature. 445:781-784 (2007).

Piccirillo et al., "Bone morphogenetic proteins inhibit the tumorigenic potential of human brain tumor-initiating cells," Nature. 444:761-765 (2006).

Lane et al., "TNF-α inhibits HIV-1 replication in peripheral blood monocytes and alveolar macrophages by inducing the production of RANTES and decreasing C-C chemokine receptor 5(CCR5) expression" J. Immunol. 163:3653-3661 (1999).

Li et al. "The relationship between tumor necrosis factor and human immunodeficiency virus gene expression in lymphoid tissue" J. Virol. 71:7080-7082 (1997).

Herbein et al. "Tumor Necrosis Factor Alpha inhibits entry of human immunodeficiency virus-type 1 into primary human macrophages: a selective role for the 75-kilodalton receptor" J. Virol. 70:7388-7397 (1996).

Mestan et al., "Antiviral effects of recombinant tumor necrosis factor in vitro" Nature 323:816-819 (1986).

Ito et al., "Antiviral effects of recombinant human tumor necrosis factor" Lympokine Res. 6:309-318 (1987).

Baharav et al., "Antiinflammatory Effect of A3 Adenosine Receptor Agonists in Murine Autoimmune Arthritis Models," J Rheumatol 32469-476 (2005).

Fishman et al., "The A3 Adenosine Receptor as a New Target for Cancer Therapy and Chemoprotection," Exp Cell Res 269:230-236 (2001).

Fishman et al., "Evidence for involvement of Wnt signaling pathway in IB-MECA mediated suppression of melanoma cells," Oncogene 21:4060-4064 (2002).

van Troostenburg et al., "Tolerability, pharmacokinetics and concentration-dependent hemodynamic effects of oral CF101, and A3 adenosine receptor agonist, in healthy young men" Int. J. Clin. Pharmacol. Ther. 42:534-542 (2004).

* cited by examiner

USE OF AN ADENOSINE A3 RECEPTOR AGONIST FOR INHIBITION OF VIRAL REPLICATION

FIELD OF THE INVENTION

The present invention is generally in the field of anti-infectives and more specifically it concerns pharmaceutical compositions and medical uses for inhibiting viral replication inside cells.

PRIOR ART

The following is a list of prior art, which is considered to be pertinent for describing the state of the art in the field of the invention. Acknowledgement of these references herein will be made by indicating the number from their list below within brackets.

1. Linden J. The FASEB J. 5:2668-2676 (1991);
2. Stiles G. L. *Clin. Res.* 38:10-18 (1990);
3. Stolfi R. L., et al. *Cancer Res.* 43:561-566 (1983);
4. Soderback U. et al. *Clin. Sci.* 81:691-694 (1994);
5. Gilbertsen R. B. *Agents actions* 22:91-98 (1987);
6. Bouma M. G. et al. *J. Immunol.* 153: 4159-4168 (1994);
7. Rozengurt E. *Exp. Cell Res.* 139:71-78 (1982);
8. Gonzales F. A., et al., PNAS USA 87:9717-9721 (1990);
9. Sandberg G. and Fredholm B. B., *Thymus* 3:63-75 (1981);
10. Pastan I. H. et al. *Annu. Rev. Biochem.* 44:491-495 (1975);
11. R. Cole and J. de Vellis. 1997. In: *Protocols for neural cell culture*. S. Fedoroff and A. Richardson (Eds.) Human Press, Totowa, N.J., pp. 117-130.
12. S. Gartner and M. Popovic. 1990. In: *Techniques on HIV research*. A Aldovini and B. D. Walker (Eds.) Stockton Press. New York, N.Y., pp. 53-70.
13. V. W. Yong and J. P. Antel, 1997. In: *Protocols for neural cell culture*. S. Fedoroff and A. Richardson (Eds.) Humana Press, Totowa, N.J., pp. 157-172.
14. U.S. Pat. No. 5,688,774.
15. U.S. Pat. No. 5,773,423.
16. U.S. Pat. No. 6,048,865.
17. WO 95/02604.
18. WO 99/20284.
19. WO 99/06053

BACKGROUND OF THE INVENTION

Human immunodeficiency viruses types 1 and 2 (HIV-1 and HIV-2) are retroviruses that cause acquired immunodeficiency syndrome (AIDS) in humans. AIDS results from low levels of CD4-positive T-lymphocytes in HIV-infected individuals.

HIV-1 infects T-lymphocytes, monocytes/macrophages, dendritic cells and microglia. All of these cells express the surface glycoprotein CD4 which serves as a receptor for HIV-1 and HIV-2. Efficient entry of HIV-1 into target cells is dependent upon binding of the viral envelope glycoprotein gp120 to CD4. In addition, several chemokine receptors function as HIV co-receptors and determine efficient infection of various cell types with HIV-1 strains. After binding, the HIV-1 envelope glycoproteins mediate fusion of viral and host cell membranes to complete the entry process. Once inside the cells, a process of viral replication occurs and through a budding process replicated viruses are released from infected cells, This eventually leads to cytolytic destruction of the infected cells. This sequence is repeated many times thereby significantly reducing the number of the target cells in the body, which is a severe and life-threatening material state often giving rise to eventual death of the infected individual.

Adenosine is a purine nucleoside present in plasma and other extracellular fluids. It is released into the extracellular space by various cell types and exerts an effect or other cells by binding to G-protein associated receptors on the cell membrane[1-2]. The interaction of adenosine with its receptors initiates signal transduction pathways, progressing mainly the adenylate cyclase effector system, which utilizes cAMP as a second messenger. G-protein associated adenosine receptors are classified into four groups referred to as A1, A2a, A2b and A3. A1 and A3 receptors are coupled with $G_i$ proteins and thus inhibit adenylate cyclase leading to a decrease in the level of intracellular cAMP. The A2a and A2b receptors are coupled to $G_s$ proteins and thus activates adenylate cyclase, thereby increasing cAMP levels[3].

Among the physiological effects of extracellular adenosine are inhibition of cytokine release, inhibition of platelet aggregation, induction of erythropoietin production and modulation of lymphocyte function[4-6]. Adenosine is also involved in the modulation of some central nervous system (CNS) functions, in wound healing, in diuresis and in controlling pain. Adenosine is capable of inducing proliferation in a wide range of normal cell types[7-10].

SUMMARY OF THE INVENTION

The present invention is based upon the finding that adenosine receptor agonists inhibit viral replication inside cells. Thus, in accordance with the invention, there is provided a method for inhibiting viral replication in cells, comprising presenting to the cells an effective amount of at least one adenosine A3 receptor agonist (A3RAg).

The agonist according to the invention is either a full or partial agonist of the adenosine $A_3$ receptor. As used herein, a compound is a "full agonist" of an adenosine $A_3$ receptor if it is able to fully inhibit adenylate cyclase ($A_3$), a compound is a "partial agoinist" of an adenosine $A_3$ receptor if it is able to partially inhibit adenylate cyclase ($A_3$).

Also provided by the invention are pharmaceutical compositions for inhibiting viral replication inside cells, comprising an effective amount of said at least one A3RAg, as well as the use of said active ingredient (i.e. the A3RAg) for the manufacture of such a pharmaceutical composition.

The invention is particularly useful, although not limited to, inhibiting the replication of HIV virus in human cells.

DETAILED DESCRIPTION OF THE INVENTION

The pharmaceutically or therapeutically "effective amount" for purposes herein is determined by such considerations as may be known in the art. The amount must be effective to achieve the desired therapeutic effect, which depends on the type and mode of treatment. As is clear to the artisan, the effective amount should be effective to reduce the rate of viral replication inside cells, to reduce the level of viral particles in clinical samples, or to obtain an improvement in the condition of an individual having a viral infection, to obtain an improvement or elimination of symptoms or any other indicators acceptable as appropriate measures by those skilled in the art. An example of an effective amount is a daily administration of an A3RAg within the range of between about 1 µg/kg body weight and about 10 mg/kg body weight. Such an amount of A3RAg is typically administered in a single daily dose although at times a daily dose may be divided into several doses administered throughout the day or at times several daily doses may be combined into a single dose to be given to the patient once every several days, particularly if administered in a sustained release formulation.

By one embodiment, the active ingredient is a nucleoside derivative. By the term "nucleoside" it is meant any compound comprising a sugar, preferably ribose or deoxyribose, or a purine or pyrimidine base or a combination of a sugar with a purine or pyrimidine base preferably bound to one another through a N-glycosyl link. The term "nucleoside derivative" will be used to denote herein, a naturally occurring nucleoside, a synthetic nucleoside or a nucleoside, which underwent chemical modifications by way of one or more insertions, deletions, exocyclic or endocyclic substitutions of one or more groups thererin or conformational modifications which provide a derivative with the desired biological effect.

According to one embodiment of the invention, the active ingredient is a nucleoside derivative of the following general formula (I):

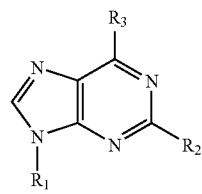

(I)

wherein $R_1$ is alkyl, hydroxyalkyl carboxyalkyl or cyanoalkyl or a group of the following general formula (II):

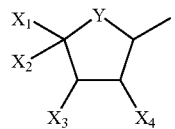

(II)

in which:

Y is oxygen, sulfur of carbon atoms;

$X_1$ is H, alkyl $R^aR^bNC(=O)$— or $HOR^c$—, wherein $R^a$ and $R^b$ may be the same or different and are selected from the group consisting of hydrogen, amino; or a substituted or unsubstituted alkyl, haloalkyl, aminoalkyl, BOC-aminoalkyl, and cycloalkyl or are joined together to form a heterocyclic ring containing two to five carbon atoms, and $R^c$ is selected from the group consisting of alkyl, amino, haloalkyl, aminoalkyl, protected aminoalkyl (e.g.-BOC aminoalkyl), and cycloalkyl;

$X_2$ is H, hydroxyl, alkylamino, alkylamido or hydroxyalkyl;

$X_3$ and $X_4$ each independently are hydrogen, hydroxyl, amino, amido, azido, halo, alkyl, alkoxy, carboxy, nitrilo, nitro, trifluoro, aryl, alkaryl, thio, ester, thioester, ether, thioether, —OCOPh, —OC(=S)OPh or both $X_3$ and $X_4$ are oxygen connected to >C=S to form a 5-membered ring, or $X_2$ and $X_3$ form the ring of formula (III):

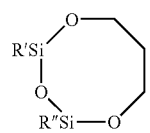

(III)

where R' and R" are independently a lower alkyl;

$R_2$ is selected from the group consisting of hydrogen, halo, alkylether, amino, hydrazido, alkylamino, alkoxy, thioalkoxy, pyridylthio, alkenyl; alkynyl, thio, and alkylthio; and $R_3$ is an —$NR_4R_5$ group, wherein $R_4$ is a hydrogen or a group selected from alkyl, substituted alkyl or aryl-NH—C(Z)-, with Z being O, S, or $NR^a$ with $R^a$ having the above meanings, and $R_5$, is a group selected from heteroaryl-$NR^a$—C(Z)-, heteroaryl-C(Z)-, alkaryl-$NR^a$—C(Z)-, alkaryl-C(Z)-, aryl-NR—C(Z)- and aryl-C(Z)-, $R^a$ and Z having the above defined meanings; or, when $R_4$ is a hydrogen, $R_5$ is R— or S-1-phenylethyl, benzyl, phenylethyl or anilide, all of the above optionally substituted in one or more positions with a substituent selected from the group consisting of alkyl, amino, halo, haloalkyl, nitro, hydroxyl, acetoamido, alkoxy, and sulfonic acid or a salt thereof;

or when $R_4$ is benzodioxanemethyl, fururyl, L-propylalanylaminobenzyl, β-alanylamino-benzyl, T-BOC-β-alanylamino-benzyl, phenylamino, carbamoyl, phenoxy or cycloalkyl, $R_5$ is a group of the following formula:

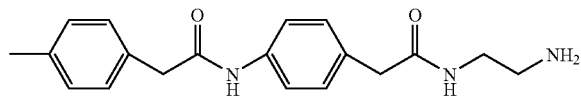

or a suitable salt of the compound defined above, e.g. a triethylammonium salt thereof.

The active ingredient is preferably a nucleoside derivative of the general formula (IV):

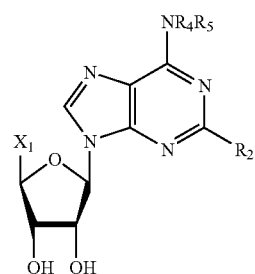

(IV)

wherein $X_1$, $R_2$ $R_4$ and $R_5$ are as defined above and

Preferred active ingredients according to this embodiment of the invention may generally be referred to as $N^6$-benzyladenosine-5'-uronamides and derivatives thereof found to be A3-selective adenosine receptor agonists. Examples for such derivatives are $N^6$-2-(4-aminophenyl)ethyladenosine (APNEA), $N^6$-(4-amino-3-iodobenzyl) adenosine-5'-(N-methyluronamide) (AB-MECA) and 1-deoxy-1-{6-[({3- iodophenyl}methyl)amino]-9H-purine-9-yl}-N-methyl-β-D-ribofuranuron-amide, the latter also referred to in the art as $N^6$-3-idobenzyl-5'-methylcarboxamidoadenosine or $N^6$-(3-idobenzyl)adenosine-5'-N-methyl-uronamide and herein above and below by the abbreviation IB-MECA. A chlorinated derivative of IB-MECA ($R_2$=Cl) also forms part of this group and is referred to herein as Cl-IB-MECA, IB-MECA and Cl-IB-MECA being currently preferred.

According to another embodiment of the invention, the active ingredient may be adenosine derivative generally referred to as $N^6$-benzyl-adenosine-5'-alkyluronamide-$N^1$-oxide or $N^6$-benzyladenosine-5'-N-dialyluron-amide-$N^1$-oxide.

Some of the above defined compounds and their synthesis procedure may be found in publications 14 to 19 listed above, incorporated herein by reference.

The hydrocarbon chains used herein may include straight or branched chains. In particular, the term "alkyl" refers to monovalent straight, branched of cyclc alkyl groups preferably having from 1-20 carbon atoms, more preferably 1-10 carbon atomes ("lower alkyl") and most preferably 1 to 6 atoms. This term is exemplified by groups such as methyl, ethyl, n-propyl, iso-propyl, n-butyl, iso-butyl, n-hexyl, and the like.

The terms "alkylene" and "lower alkylene" refer to divalent radicals of the corresponding alkane. Further, as used herein, other moieties having names derived from alkanes, such as alkoxyl, alkanoyl, alkenyl, cycloalkenyl, etc. when modified by "lower", have carbon chains of ten or less carbon atoms. In those cases where the minimum number of carbons are greater than one, e.g., alkenyl (minimum of two carbons) and cycloalkyl, (minimum of three carbons), it is to be understood that "lower" means at least the minimum number of carbons.

As used herein, the term "substituted alkyl" refers to an alkyl group, having from 1 to 4 substituents, and preferably 1 to 3 substituents as defined above. As used herein, other moieties having the prefix "substituted" are intended to include one or more of the substituents listed above.

As used herein, the term "alkoxy" refers to the group "alkyl-O—" , where alkyl is as defined above.

As used herein, the term "alkenyl" refers to alkenyl groups preferably having from 2 to 10 carbon atoms and more preferably 2 to 6 carbon atoms and having at least 1 and preferably from 1-2 sites of alkenyl unsaturation while the term "alkynyl" refers to alkynyl groups preferably having from 2 to 10 carbon atoms and more preferably 2 to 6 carbon atoms and having at least 1 and preferably from 1-2 sites of alkynyl unsaturation.

As used herein, the term "aryl" refers to an unsaturated aromatic carbocyclic group of from 6 to 14 carbon atoms having a single ring (e.g., phenyl) or multiple condensed (fused) rings (e.g., naphthyl or anthryl). Preferred aryls include phenyl, naphthyl and the like. Unless otherwise stated by the definition for the aryl substituent, such aryl groups can optionally be substituted with from 1 to 5 substituents and preferably 1 to 3 substituents such as those provided above.

As used herein, the term "cycloalkyl" refers to cyclic alkyl groups of from 3 to 12 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like.

As used herein, the term "heteroaryl" refers to an aromatic carbocyclic group of from 1 to 15 carbon atoms and 1 to 4 heteroatoms selected from the group consisting of oxygen, nitrogen and sulfur within at least one ring (if there is more than one ring). Unless otherwise stated such heteroaryl groups can be optionally substituted with from 1 to 5 substituents and preferably 1 to 3 substituents as indicated above.

As to any of the above groups that contain 1 or more substituents, it is understood, of course, that such groups do not contain any substitution or substitution patterns which are sterically impractical and/or synthetically non-feasible.

At times, the above defined A3RAg, being the active ingredient, may contain a protecting groups or blocking groups. The term "protecting group" or "blocking group" refers to any group which when bound to one or more hydroxyl, amino or carboxyl groups of the compounds prevents reaction from occurring at these groups and which protecting group can be removed by conventional chemical or enzymatic steps to reestablish the hydroxyl, amino or carboxyl group. Preferred removable amino blocking groups include conventional substituents such as t-butyoxycarbonyl (t-BOC) (indicated above) as well as others such as, benzyloxycarbonyl (CBZ), and the like which can be removed by conventional conditions compatible with the nature of the product.

The A3RAg in accordance with the invention may be as defined above or may be in the form of salts or solvates thereof, in particular physiologically acceptable salts and solvates thereof. Further, when containing one or more asymmetric carbon atoms, the active ingredient may include isomers and diastereoisomers of the above active ingredients or mixtures thereof.

Pharmaceutically acceptable salts of the above active ingredients include those derived from pharmaceutically acceptable inorganic and organic acids. Examples of suitable acids include hydrochloric, hydrobromic, sulphoric, nitric, perchloric, fumaric, maleic, phosphoric, glycollic, lactic, salicylic, succinic, toluene-p-sulfonic, tartaric, acetic, citric, methanesulfonic, formic, benzoic, malonic, naphthalene-2-sulfonic and benzenesulfonic acids.

The A3RAg may be administered as a non-active substance (e.g. pro-drug) and be made active only upon further modification/s by a natural process at a specific site in the subject. In any case, the derivative will be such that the therapeutic functionality of the pharmaceutical composition of the invention, is preserved. Such pro-drugs are also encompassed by the term "active ingredient" as used herein. Similarly, the term "A3RAg" should be understood as encompassing pro-drugs which, although a priori, lack the agonistic activity, become active in vivo.

To choose an adenosine A3 receptor agonist to be used in accordance with the invention, candidate components may be screened for such compounds which have an ability to inhibit viral replication in a manner resembling that of IB-MECA or CI-IB-MECA. A suitable screen is an in vitro assay of the kind described in the Experiments Results Section below. However, a variety of other assays known per se may also be used.

The pharmaceutical composition of the invention may comprise the A3RAg as such, but may be combined with other ingredients which may be a pharmaceutically acceptable carrier, diluent, excipient, additive and/or adjuvent, as known to the artisan, e.g. for the purposes of adding flavors, colors, lubrication or the like to the pharmaceutical composition. Evidently, the pharmaceutically acceptable carrier/s, diluent/s, excipient/s, additive/s employed according to the invention generally refer to inert, non-toxic solid or liquid fillers, diluents or encapsulating materials which preferably do not react with the compounds within the composition of the invention.

Many A3RAgs are bioavailable when orally administered. Thus, depending on the active ingredient, the pharmaceutical composition of the invention may be formulated for oral administration. Such an oral composition may further comprise a pharmaceutically acceptable carrier, diluent, excipient, additive or adjuvant suitable for oral administration.

The pharmaceutical compositions of the invention are administered and dosed in accordance with good medical practice, taking into account the clinical condition of the individual patient, the site and method of administration, scheduling of administration, patient's age, sex, body weight and other factors known to medical practitioners.

The composition of the invention may be administered in various ways. It can be administered orally, subcutaneously or parenterally including intravenous, intraarterial, intramuscular, intraperitoneally or by intranasal administration, as well as by intrathecal and infusion techniques known to the man versed in the art.

The treatment has an overall length contingent to the length of the disease process and active agent effectiveness. The therapeutic regimen may involve single doses or multiple doses over a period of several days or more.

When administering the compositions of the present invention parenterally, it will generally be formulated in a unit dosage injectable form (solution, suspension, emulsion). The pharmaceutical formulation suitable for injection includes sterile aqueous solutions or dispersions and sterile powders for reconstitution into sterile injectable solutions or dispersions. The carrier employed can be a solvent or dispersing medium containing, for example, water, ethanol, polyol (for example, glycerol, propylene glycol, lipid polyethylene glycol and the like), suitable mixtures thereof and vegetable oils.

Non-aqueous vehicles such as cottonseed oil, sesame oil, olive oil, soybean oil, corn oil, sunflower oil, or peanut oil and ester, such as isopropyl myristate, may also at times be used as solvent systems for the active ingredient.

Additionally, various additives which enhance the stability, sterility and isotonicity of the compositions, including antimicrobial preservatives, antioxidants, chelating agents and buffers can be added. Prevention of the action of microorganisms can be ensured by various antibacterial and antifungal agents, for example, parabens, chlorobutanol, phenol, sorbic acid and the like.

For the purpose of oral administration, the active ingredient may be formulated in the form of tablets, suspensions, solutions, emulsions, capsules, powders, syrups and the like, are usable and may be obtained by techniques well known to the pharmacists.

The present invention will now be described by way of example with reference to the experimental results below and to the accompanying Figures. It is to be understood, that the terminology which has been used is intended to be in the nature of words of description rather than limitation.

While the foregoing description describes in detail only a few specific embodiments of the invention, it will be understood by those skilled in the art that the invention is not limited thereto and that other variations in form and details may be possible without departing from the scope and spirit of the invention herein disclosed.

EXPERIMENTAL RESULTS

Materials and Methods:

Preparation of Primary Human Fetal Astrocytes and Microglia.

Purified primary human fetal astrocytes and microgial cells were prepared from 16 to 20 week old human fetal brain tissue by a modified procedure based on the methods of Cole and de Vellis[11], and Yong and Ante[13]. Brain tissue was washed in ice-cold Hank's Balanced Salt Solution (HBSS) containing the antibiotics gentamycin and amphotericin B. Blood vessels and meninges were removed and the tissue was minced into small pieces. After mincing, the tissue was enzymatically dissociated by incubation in 0.05% trypsin and mechanically disrupted by passing several times over a 75 μm nylon mesh filter. The resulting single cell suspension was washed, pelleted and plated at a density of $2\text{-}10 \times 10^6$ cells per 162 cm$^2$ flask in DMEM:F12 containing 10% fetal calf serum, insulin, gentamycin, and L-glutamine. After 7-10 days of growth, microglial cells were isolated by placement on rotary shaker at 200 rpm in a 37° C. incubator overnight. The non-adherent cells were removed and allowed to attach to a new flask for 1 to 3 h. Following attachment, the cells were washed and refed with media containing 10% fetal calf serum, insulin, gentamycin, L-glutamine, and NI supplement. Astrocytes were subcultured from adherent cells in media containing 15% fetal calf serum, insulin, gentamycin, and L-glutamine and contaminating microglia were removed by repeated rotary shaking. Cultured astrocytic and microglial cells were plated at a density of 2.5×105 per well into 6 well plates for subsequent infection.

Preparation of HIV-1 Virus

Brain derived primary HIV-1 isolates SF162 and JR-FL were cultured in human peripheral blood mononuclear cells (PBMC) essentially as described by Gartner and Popovic[12]. PBMC were isolated from human buffy coat by fico gradient and plated at a density of $2.5 \times 10^6$ per ml in RPMI containing 10% fet calf serum and gentamycin. Cells were stimulated by the addition of 5 ug/ml phytohemagglutinin (PHA) for 48 h. After stimulation, cells were infected will either SF162 or JR-FL and cultured for 7 to 10 days until high titres of HIV-1 we detected in the supernatant by p24 ELISA assay. When viral production was optimal, the cells were pelleted, the supernatant containing HIV-1 was aliquoted and stored at −70° C. until use. P24 ELISA assay was performed on an aliquoted stock to determine the viral titre.

Infection of Primary Human Fetal Astrocytic and Microglial Cells and Treatment with Cl-IB-MECA.

$2.5 \times 10^5$ microglial or astrocytic cells were plated per well into 6-we plates. The next day, cells were washed and refed with fresh medium. $2 \times 10^4$ p2units of either SF 162 or JR-FL virus was added per well in a total of 1 ml of vir inoculum. In control experiments, the virus was not added. Cells were incubated with virus overnight at 37° C., washed extensively with PBS, and refed with 2 π fresh medium. Cultures were treated with IB-MECA or Cl-IB-MECA at concentration of 0.01 μM every 24 hours. 500 μl of medium were removed at the indicated times following infection and stored at −70° C. for later analysis. Each time medium was removed, a volume amount of fresh medium was added. In control experiments IB-MECA and Cl-IB-MECA were omitted.

p24 ELISA Assay.

ELISA assay to detect the HIV-1 viral core protein, p24, was performed of 50 μl of the collected supernatant utilizing the commercially available p24 ELISA Kit (NEN/Dupont) according to the manufacturer's instructions.

Results

A seen in Tables 1 to 3, the amount of p24 protein present in culture medium collected from HIV infected cells is significantly reduced in HIV infected cells treated with IB-MECA (HIV and IB-MECA) or Cl-IB-MECA (HIV and CI IB-MECA) in comparison to controls not related with either IB-MECA or Cl-IB-MECA, (HIV).

Table 1 shows the effect of IB-MECA and Cl-IB-MECA on HIV replication in JR-FL infected astroglial cells, wherein p 24 protein (pg/mL) was measured in medium from cell cultures 5 days after HIV infection.

Table 2 shows the effect of IB-MECA and Cl-IB-MECA on HIV replication in SF162 infected astroglia, wherein p 24 protein (pg/mL) was measured as indicated above.

Table shows the effect of IB-MECA and Cl-IB-MECA on HIV replication in SF126 infected microglia/SF, wherein p 24 protein (pg/mL) was measured in medium from cell cultures 5 days and 10 days after HIV infection.

TABLE 1

Astroglia/JR-FL

| Treatment | p24 pg/mL Day 5 |
|---|---|
| No HIV | 12.64 |
| HIV | 22.83 |
| HIV and IB-MECA 0.01 | 3.02 |
| HIV and Cl-IB-MECA 0.01 | 8.45 |

TABLE 2

Astroglia/SF-162

| Treatment | p24 pg/mL Day 5 |
|---|---|
| No HIV | −12.96 |
| HIV | 313.38 |
| IB-MECA 0.01 | 137.58 |
| Cl-IB-MECA 0.01 | 288.77 |

TABLE 3

Microglia/SF

| | p24 pg/mL | |
|---|---|---|
| | Day 5 after infection | Day 10 after infection |
| No HIV | −12.64 | −12.64 |
| HIV | 267.99 | 209.18 |
| IB-MECA 0.01 | 81.33 | 62.79 |
| IB-MECA 0.1 | 82.29 | 54.80 |
| Cl-IB-MECA 0.01 | 127.03 | 111.05 |
| Cl-IB-MECA 0.0.1 | 10.81 | 80.37 |

The invention claimed is:

1. A method for inhibiting replication of a virus in cells comprising contacting the cells with an effective amount of at least one adenosine A3 receptor agonist (A3RAg).

2. The method of claim 1, wherein the virus is an HIV.

3. The method of claim 1, wherein said A3RAg is a nucleotide derivative of the following general formula (I):

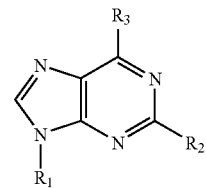

(I)

wherein $R_1$ is alkyl, hydroxyalkyl, carboxyalkyl or cyanoalkyl or a group of the following general formula (II):

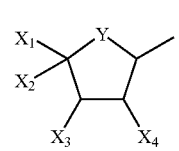

(II)

in which:
Y is oxygen, sulfur, or $CH_2$;
$X_1$ is H, alkyl, $R^a R^b NC(=O)$— or $HOR^c$—,
wherein $R^a$ and $R^b$ may be the same or different and are selected from the group consisting of hydrogen, amino, a substituted or unsubstituted alkyl, haloalkyl, aminoalkyl, protected-aminoalkyl, and cycloalkyl, or are joined together to form a heterocyclic ring containing two to five carbon atoms, and $R^c$ is selected from the group consisting of alkyl, amino, haloalkyl, aminoalkyl, BOC-aminoalkyl, and cycloalkyl;
$X_2$ is H, hydroxyl, alkylamino, alkylamido or hydroxyalkyl;
$X_3$ and $X_4$ each independently are hydrogen, hydroxyl, amino, amido, azido, halo, alkyl, alkoxy, carboxy, nitrilo, nitro, trifluoro, aryl, alkaryl, thio, ester, thioester, ether, thioether, —OCOPh, or —OC(=S)OPh or both $X_3$ and $X_4$ are oxygen connected to >C=S to form a 5-membered ring, or $X_2$ and $X_3$ form the ring of formula (III):

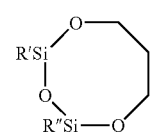

(III)

where R' and R'" are independently alkyl;
$R_2$ is selected from the group consisting of hydrogen, halo, alkylether, amino, hydrazido, alkylamino, alkoxy, thioalkoxy, pyridylthio, alkenyl; alkynyl, thio, and alkylthio; and
$R_3$ is a —$NR_4R_5$ group with $R_4$ being hydrogen, alkyl, substituted alkyl or aryl-NH—C(Z)—, with Z being O, S, or $NR^a$ with $R^a$ having the above meanings, and $R_5$ is a group selected from the group consisting of heteroaryl-$NR^a$— C(Z)—, heteroaryl-C(Z)—, alkaryl-$NR^a$—C(Z)—, alkaryl-C(Z)—, aryl-NR—C(Z)—and aryl-C(Z)—, with $R^a$ and Z having the above defined meanings; or, when $R_4$ is a hydrogen, $R_5$ is R— or S-1-phenylethyl, benzyl, phenylethyl or anilide, all of the above optionally substituted in one or more positions with a substituent selected from the group consisting of alkyl, amino, halo, haloalkyl, nitro, hydroxyl, acetamido, alkoxy, and sulfonic acid or a salt thereof; or when $R_4$ is benzodioxanemethyl, fururyl, L-propylalanylaminobenzyl, β-alanylaminobenzyl, T-protected-β-alanylaminobenzyl, phenylamino, carbamoyl, phenoxy or cycloalkyl, then $R_5$ is a group of the following formula:

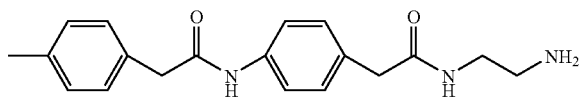

or a suitable salt of the compound defined above.

4. The method of claim 3, wherein said A3RAg is a nucleoside derivative of the general formula (IV):

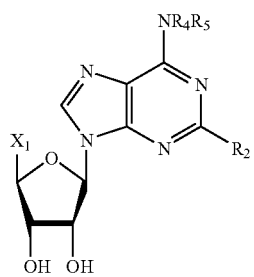

(IV)

wherein $X_1$, $R_2$ $R_4$ and $R_5$ are as defined in claim 3.

5. The method of claim 4, wherein the active ingredient is an $N^6$-benzyladenosine-5'-uronamide.

6. The method of claim 5, wherein said A3RAg is selected from the group consisting of $N^6$-2-(4-aminophenyl)ethyladenosine (APNEA), $N^6$-(4-amino-3-iodobenzyl) adenosine-5'-(N-methyluronamide) (AB-MECA) and 1-deoxy-1-{6-[({3-iodophenyl}methyl) amino]-9H-purine-9-yl}-N-methyl-β-D-ribofuranuronamide (IB-MECA) and 2-chloro-$N^6$-(3-iodobenzyl)-adenosine-5'-N-methyl-uronamide (Cl-IB-MECA).

7. The method of claim 6, wherein said A3RAg is IB-MECA or Cl-IB-MECA.

8. A method for inhibiting replication of a virus in cells of an individual in need of treatment for viral infection, comprising administering to the individual an effective amount of at least one adenosine A3 receptor agonist (A3RAg).

9. The method of claim 8, wherein the virus is an HIV.

10. The method of claim 8, wherein the at least one A3RAg is a nucleotide derivative of the following general formula (I):

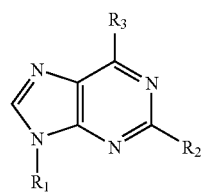

(I)

wherein $R_1$ is alkyl, hydroxyalkyl, carboxyalkyl or cyanoalkyl or a group of the following general formula (II):

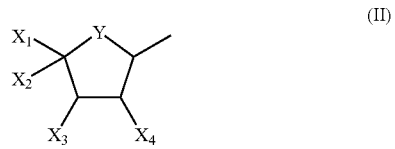

(II)

in which:

Y is oxygen, sulfur, or $CH_2$;

$X_1$ is H, alkyl, $R^aR^bNC(=O)$— or $HOR^c$—, wherein $R^a$ and $R^b$ may be the same or different and are selected from the group consisting of hydrogen, amino, a substituted or unsubstituted alkyl, haloalkyl, aminoalkyl, protected-aminoalkyl, and cycloalkyl, or are joined together to form a heterocyclic ring containing two to five carbon atoms, and $R^c$ is selected from the group consisting of alkyl, amino, haloalkyl, aminoalkyl, BOC-aminoalkyl, and cycloalkyl;

$X_2$ is H, hydroxyl, alkylamino, alkylamido or hydroxyalkyl;

$X_3$ and $X_4$ each independently are hydrogen, hydroxyl, amino, amido, azido, halo, alkyl, alkoxy, carboxy, nitrilo, nitro, trifluoro, aryl, alkaryl, thio, ester, thioester, ether, thioether, —OCOPh, or —OC(=S)OPh or both $X_3$ and $X_4$ are oxygen connected to >C=S to form a 5-membered ring, or $X_2$ and $X_3$ form the ring of formula (III):

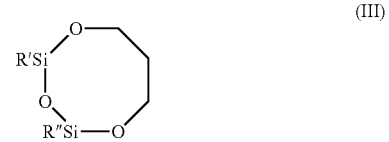

(III)

where R' and R" are independently alkyl;

$R_2$ is selected from the group consisting of hydrogen, halo, alkylether, amino, hydrazido, alkylamino, alkoxy, thioalkoxy, pyridylthio, alkenyl; alkynyl; thio, and alkylthio; and $R_3$ is a —$NR_4R_5$ group with $R_4$ being hydrogen, alkyl, substituted alkyl or aryl-NH—C(Z)—, with Z being O, S, or $NR^a$ with $R^a$ having the above meanings, and $R_5$ is a group selected from the group consisting of heteroaryl-$NR^a$— C(Z)—, heteroaryl-C(Z)—, alkaryl-$NR^a$—C(Z)—, alkaryl-C(Z)—, aryl-NR—C(Z)— and aryl-C(Z)—, with $R^a$ and Z having the above defined meanings; or, when $R_4$ is a hydrogen, $R_5$ is R— or 5-1-phenylethyl, benzyl, phenylethyl or anilide, all of the above optionally substituted in one or more positions with a substituent selected from the group consisting of alkyl, amino, halo, haloalkyl, nitro, hydroxyl, acetamido, alkoxy, and sulfonic acid or a salt thereof; or when $R_4$ is benzodioxanemethyl, fururyl, L-propylalanylaminobenzyl, β-alanylaminobenzyl, T-protected-β-alanylaminobenzyl, phenylamino, carbamoyl, phenoxy or cycloalkyl, then $R_5$ is a group of the following formula:

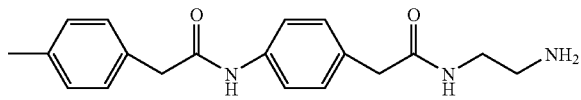

or a suitable salt of the compound defined above.

11. The method of claim 10, wherein the at least one A3RAg is a nucleoside derivative of the general formula (IV):

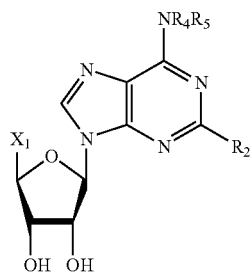

(IV)

wherein $X_1$, $R_2$ $R_4$ and $R_5$ are as defined in claim 10.

12. The method of claim 11, wherein the at least one A3RAg is an $N^6$-benzyladenosine-5'-uronamide.

13. The method of claim 12, wherein the at least one A3RAg is selected from the group consisting of $N^6$-2-(4-aminophenyl)ethyladenosine (APNEA), $N^6$-(4-amino-3-iodobenzyl) adenosine-5'-(N-methyluronamide) (AB-MECA) and 1-deoxy-1-{6-[({3-iodophenyl}methyl)amino]-9H-purine-9-yl}-N-methyl-β-D-ribofuranuronamide (IB-MECA) and 2-chloro-$N^6$-(3-iodobenzyl)-adenosine-5'-N-methyluronamide (Cl-IB-MECA).

14. The method of 3, wherein said suitable salt of the compound is a triethylammonium salt.

15. The method of claim 13, wherein the at least one A3RAg is IB-MECA or Cl-IB-MECA.

16. The method of claim 8, wherein said suitable salt of the compound is a triethylammonium salt.

* * * * *